(12) United States Patent
Palomba et al.

(10) Patent No.: US 10,571,407 B2
(45) Date of Patent: *Feb. 25, 2020

(54) DETERMINING INFORMATION FOR DEFECTS ON WAFERS

(71) Applicant: KLA-Tencor Corporation, Milpitas, CA (US)

(72) Inventors: Stefano Palomba, San Jose, CA (US); Pavel Kolchin, Fremont, CA (US); Mikhail Haurylau, San Jose, CA (US); Robert M. Danen, Pleasanton, CA (US); David W. Shortt, Los Gatos, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/400,644

(22) Filed: May 1, 2019

(65) Prior Publication Data

US 2019/0257768 A1   Aug. 22, 2019

Related U.S. Application Data

(63) Continuation of application No. 14/511,067, filed on Oct. 9, 2014, now Pat. No. 10,317,347.

(60) Provisional application No. 61/899,079, filed on Nov. 1, 2013.

(51) Int. Cl.
*G01N 21/95* (2006.01)
*G01N 21/64* (2006.01)
*G01N 21/94* (2006.01)

(52) U.S. Cl.
CPC ......... *G01N 21/9501* (2013.01); *G01N 21/64* (2013.01); *G01N 21/6489* (2013.01); *G01N 21/94* (2013.01); *G01N 2201/0612* (2013.01); *G01N 2201/12* (2013.01)

(58) Field of Classification Search
CPC ..... G01N 21/9501; G01N 21/64; G01N 21/94
See application file for complete search history.

(56) References Cited

U.S. PATENT DOCUMENTS 6,422,994 B1 *   7/2002   Kaneko ............. A61B 1/00009
                                                      600/160

* cited by examiner

*Primary Examiner* — Marcus H Taningco
(74) *Attorney, Agent, or Firm* — Ann Marie Mewherter (57) ABSTRACT

Systems and methods for determining information for defects on a wafer are provided. One system includes an illumination subsystem configured to direct light having one or more illumination wavelengths to a wafer. The one or more illumination wavelengths are selected to cause fluorescence from one or more materials on the wafer without causing fluorescence from one or more other materials on the wafer. The system also includes a detection subsystem configured to detect only the fluorescence from the one or more materials or to detect non-fluorescent light from the wafer without detecting the fluorescence from the one or more materials. In addition, the system includes a computer subsystem configured to determine information for defects on the wafer using output generated by the detection subsystem responsive to the detected fluorescence or the detected non-fluorescent light.

20 Claims, 2 Drawing Sheets

DETERMINING INFORMATION FOR DEFECTS ON WAFERS

BACKGROUND OF THE INVENTION

1. Field of the Invention

The present invention generally relates to systems and methods for determining information for defects on wafers.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

Some currently used inspection systems are configured to detect or suppress fluorescence signals from defects or wafer background. However, such tools generally do not have much flexibility in the wavelengths of light used for excitation and the wavelengths of emission that are detected by the tools. For example, some such tools are configured to illuminate a wafer with a single wavelength and include a limited number of spectral filters in the optical collection path. In addition, many such tools are not configured for inspection of patterned wafers containing rectilinear or other patterns that scatter light strongly or can otherwise cause noise in the output of the tools that increases the difficulty of detecting defects on the wafers.

Accordingly, it would be advantageous to develop methods and systems for determining information for defects on wafers that do not have one or more disadvantages described above.

SUMMARY OF THE INVENTION

The following description of various embodiments is not to be construed in any way as limiting the subject matter of the appended claims.

One embodiment relates to a system configured to determine information for defects on a wafer. The system includes an illumination subsystem configured to direct light having one or more illumination wavelengths to a wafer. The one or more illumination wavelengths are selected to cause fluorescence from one or more materials on the wafer without causing fluorescence from one or more other materials on the wafer. The system also includes a detection subsystem configured to detect only the fluorescence from the one or more materials or to detect non-fluorescent light from the wafer without detecting the fluorescence from the one or more materials. In addition, the system includes a computer subsystem configured to determine information for defects on the wafer using output generated by the detection subsystem responsive to the detected fluorescence or the detected non-fluorescent light. The system may be further configured as described herein.

Another embodiment relates to a method for determining information for defects on a wafer. The method includes directing light having one or more illumination wavelengths to a wafer. The one or more illumination wavelengths are selected to cause fluorescence from one or more materials on the wafer without causing fluorescence from one or more other materials on the wafer. The method also includes detecting only the fluorescence from the one or more materials or detecting non-fluorescent light from the wafer without detecting the fluorescence from the one or more materials. In addition, the method includes determining information for defects on the wafer using output responsive to the detected fluorescence or the detected non-fluorescent light.

Each of the steps of the method described above may be further performed as described herein. In addition, the method described above may include any other step(s) of any other method(s) described herein. Furthermore, the method described above may be performed by any of the systems described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to determine information for defects on a wafer. For example, the systems described herein can be used for defect detection and classification based on fluorescence detection from patterned wafers. In addition, the embodiments provide ways to enhance defect detection, characterization, and imaging for patterned wafers by the collection or rejection of fluorescence emitted by defects or patterns under short wavelength excitation.

The system includes an illumination subsystem configured to direct light having one or more illumination wavelengths to a wafer. For example, in the system embodiment shown in FIG. 1, the illumination subsystem of system 100 includes light source 102, which may include any of the light sources described herein. Light generated by light source 102 may be directed through one or more spectral filters 104 of the illumination subsystem. Spectral filter(s) 104 may be configured as described further herein. The illumination subsystem may also include beamsplitter 106 that is configured to reflect light from the spectral filter(s) to objective 108 of the illumination subsystem. Beamsplitter 106 and objective 108 may be further configured as described herein. Objective 108 is configured to focus light having the one or more illumination wavelengths from the beamsplitter to wafer 110, which may include any of the wafers described herein.

The one or more illumination wavelengths are selected to cause fluorescence from one or more materials on the wafer without causing fluorescence from one or more other materials on the wafer. In this manner, the illumination wavelength range can be adjusted depending on the wafer materials, the patterned structures, and defect composition. The one or more materials may include fluorescing materials such as resist, bottom anti-reflecting coating (BARC), silicon nitride, silicon dioxide, and potentially other materials capable of converting the wavelength of incident light to alternate wavelengths through mechanisms in addition to fluorescence.

In one embodiment, the one or more materials include one or more sacrificial fluorescing materials not used for fabricating devices on the wafer. For example, the one or more materials may include sacrificial fluorescing materials (e.g., resist or BARC) that are used to "decorate" a patterned wafer and that can be removed from the wafer after inspection. In this manner, the sacrificial fluorescing material(s) may not be materials that will form a device structure on the wafer or materials that are used to form a device structure on the wafer. For example, resists are materials that are not normally used to form device structures on wafers while silicon dioxide is a material that is normally used to form device structures on wafers. In other words, resists are materials that do not form final structures in a device while silicon dioxide materials do form final device structures. However, materials such as resists and BARC can be "sacrificial fluorescing materials" as that term is used herein when they are only deposited on wafers to aid in inspection and are removed from the wafers after inspection has been completed. The sacrificial materials may also include materials that are deposited on the wafer, conform to defects, and mask out lower layer structures. The one or more sacrificial materials may also include materials deposited on wafers as described in U.S. Patent Application Publication No. 2012/0113416 by Lange et al. published on May 10, 2012, which is incorporated by reference as if fully set forth herein.

In one embodiment, the illumination subsystem includes a broadband light source and one or more spectral filters positioned in a path of light from the broadband light source. For example, light source 102 shown in FIG. 1 may be a broadband light source, and one or more spectral filters 104 may be positioned in a path of light from the broadband light source. Therefore, the system may include a broadband source with a selectable wavelength range for illumination through wavelength dependent filters. For example, the wavelength(s) directed to the wafer may be altered by changing or removing the spectral filter(s) positioned in the path of the light from the light source. In this manner, the system may be configured to have flexible illumination wavelength(s) that can be varied depending on the materials on the wafer, the fluorescing properties of those materials, and the fluorescing properties of any defects of interest.

Figure 1:
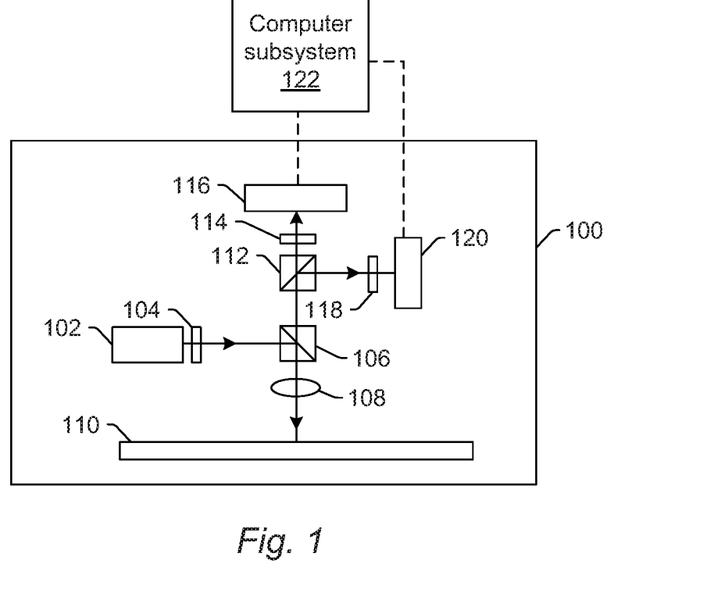
FIGS. 1-2 are schematic diagrams illustrating side views of various embodiments of a system for determining information for defects on a wafer.

The systems described herein may also incorporate narrower or modified bandpass filters into the illumination subsystem. In one such embodiment, the one or more spectral filters include one or more interference filters. For example, spectral filter(s) 104 may be interference filter(s). In this manner, the system may include a broadband source with a selectable wavelength range for illumination through interference filters. In addition, a well-defined and selectable illumination wavelength band is preferred, with a reduction of radiation outside the excitation band of at least 7-9 orders of magnitude, and is achievable by the current interference filtering technology available on the market. These filters can complement or replace bandpass filters currently being used in tools. The interference filters can be installed on currently used mechanical assemblies or new mechanical assemblies.

In another embodiment, the illumination subsystem includes one or more narrowband light sources. In an additional embodiment, the illumination subsystem includes one or more laser light sources. The narrowband and/or laser light sources may include any suitable such light sources known in the art. For example, such light sources may include one or more diode lasers, diode-pumped solid state (DPSS) lasers, gas lasers, etc. In addition, the illumination subsystems described herein may include any number of broadband, narrowband, and laser light sources in any suitable combination. Furthermore, as described further herein, the light sources may be quasi-monochromatic light sources. Any of the light sources and illumination subsystem configurations described herein may be included in an inspection system having any suitable configuration (e.g., bright field (BF), dark field (DF), BF and DF, etc.). In one particular example, the illumination subsystem may include only one laser source in a BF inspection system. In another example, an illumination subsystem may include multiple laser sources. Therefore, many different combinations of light sources and inspection system configurations are possible and may be selected depending on, for example, the wafer and/or defect characteristics.

In additional embodiments, the illumination subsystem is configured to direct light having one or more illumination angles and/or one or more illumination polarizations to the wafer, and the one or more illumination angles and/or one or more illumination polarizations are selected to cause more fluorescence, scattered light, or reflected light from the one or more materials on the wafer than from the one or more other materials on the wafer. In other words, the illumination subsystem may be configured to illuminate the wafer with light having polarization(s) and at angle(s) that selectively cause fluorescence or other light from the one or more materials. For instance, different wafer structures may respond differently to light incident from different illumination directions and/or having different polarizations. For example, light having a certain illumination direction, or set of directions, or a certain polarization may penetrate more deeply into a wafer structure and better detect a defect at the bottom of a trench. Alternatively, a certain illumination direction or polarization may not penetrate so deeply and be better suited to detect surface defects. Since the discrimination of defects from background using the various materials' fluorescence properties is a goal of the embodiments described herein, one can see that the combination of illumination direction, polarization, and fluorescence may be important. In other words, the fluorescence techniques described herein may be enhanced if the correct illumination parameters are chosen to complement the desired fluorescence effect.

The illumination subsystem may be configured in a number of different ways for selective illumination angle and/or polarization. For example, the illumination angle may be altered or selected by changing a position of a light source of the illumination subsystem or by controlling one or more other elements of the illumination subsystem that affect the illumination angle. The illumination angle that is altered or selected in the embodiments described herein may be the polar angle and/or the azimuthal angle of the incident light. In addition, the illumination polarization may be selected by selecting a light source that emits light having the selected polarization or by including one or more polarization selection/alteration/filtering elements in the path of the light emitted by the light source.

The system also includes a detection subsystem configured to detect only the fluorescence from the one or more materials or to detect non-fluorescent light from the wafer without detecting the fluorescence from the one or more materials. In this manner, fluorescing defects can be distinguished from non-fluorescing background, and noisy non-fluorescing layers can be filtered out, by collecting only long wavelength light. In the embodiment shown in FIG. 1, the detection subsystem includes objective 108 configured to collect light from wafer 110. In this embodiment, the collected light may include specularly reflected light. However, the collected light may alternatively or additionally include scattered light. The detection subsystem may also include beamsplitter 106 configured to transmit the light collected by the objective lens.

In some cases, the detection subsystem may include beamsplitter 112 configured to transmit light having one or more wavelengths of the light from the wafer, collected by the objective, and transmitted by beamsplitter 106. The detection subsystem may also include one or more bandpass filters 114 that may be configured as described further herein and may transmit light having one or more selected wavelengths. One or more of beamsplitter 106, beamsplitter 112, and bandpass filter(s) 114 may be configured to selectively transmit light having one or more selected wavelengths and to reflect or otherwise block light that does not have the one or more selected wavelengths out of the detection path of the detection subsystem such that they are not detected by detector 116. The one or more selected wavelengths may include wavelengths at which one or more materials on the wafer may fluoresce or wavelengths other than those at which one or more materials on the wafer may fluoresce. In this manner, the detector of the detection subsystem may detect only the fluorescence from the one or more materials or non-fluorescent light from the wafer without detecting the fluorescence from the one or more materials.

In some instances, the detection subsystem may also include one or more bandpass filters 118 and detector 120. In the configuration shown in FIG. 1, light reflected by beamsplitter 112 is directed to one or more bandpass filters 118, and light transmitted by the one or more bandpass filters is detected by detector 120. Bandpass filter(s) 118 and detector 120 may be further configured as described herein. Beamsplitter 112 may be configured to transmit light having one or more first wavelengths and to reflect light having one or more second wavelengths different than the first wavelength(s). In this manner, detectors 116 and 120 may detect light having different wavelengths.

In one embodiment, the illumination and detection subsystems include a common objective lens and a common dichroic mirror or beamsplitter, and the common objective lens and the common dichroic mirror or beamsplitter are configured to direct the light from a light source of the illumination subsystem to the wafer and to direct the fluorescence or the non-fluorescent light from the wafer to a detector of the detection subsystem. For example, as shown in FIG. 1, the illumination and detection subsystems may both include objective 108 making it a common objective lens and beamsplitter 106 making it a common dichroic mirror or beamsplitter. As described above, objective 108 and beamsplitter 106 are configured to direct the light from light source 102 of the illumination subsystem to wafer 110 and to direct the fluorescence or the non-fluorescent light from the wafer to detector 116 and/or detector 120 of the detection subsystem. In this manner, in a fluorescence configuration, light of the excitation wavelength is focused on the specimen through the objective lens after being reflected by an appropriate dichroic mirror or beamsplitter. The fluorescence emitted by the specimen can then be focused to the detector(s) by the same objective and through the same dichroic mirror or beamsplitter. In this way, a relatively high resolution fluorescence image at the selected detection wavelength band and excited by a particular excitation wavelength range can be generated. In addition, any beamsplitters described herein or used in currently available inspection systems can be replaced with dichroic mirrors that reflect certain wavelength bands of light and transmit the corresponding out of band light. Such configurations could increase the amount of light delivered to the wafer and increase the purity of the detected fluorescence signal, rejecting even more of the background generated by the scattered and fluorescence signals outside the spectral band of interest.

In one embodiment, one or more wavelengths of the fluorescence or the non-fluorescent light detected by the detection subsystem are selected by altering one or more parameters of the detection subsystem based on the one or more materials, the defects, the wafer, or some combination thereof. Therefore, like the illumination wavelength range, the detection wavelength range can be adjusted depending on the wafer materials, the patterned structures, and defect composition. The wavelength(s) detected by the detection subsystem may be altered as described herein (e.g., using bandpass filter(s)) or in any other suitable manner known in the art.

In some embodiments, the detection subsystem includes one or more bandpass filters positioned in a path of the fluorescence or the non-fluorescent light from the wafer, and the one or more bandpass filters are configured to control whether the fluorescence or the non-fluorescent light is detected by the detection subsystem. The detection may be preferably performed by inserting specific bandpass filters (such as bandpass filters 114 and/or 118 shown in FIG. 1) with relatively high transmissivity in the desired band and relatively high optical rejection outside the same band (i.e., high out of band extinction) into the imaging or detection path. For example, bandpass filters between the dichroic mirror or beamsplitter described above and the detector can separate excitation light from fluorescent light. Alternatively, fluorescence from a regular wafer pattern could be excluded from the detected image by inserting into the imaging path a bandpass filter centered on the excitation wavelength, which can reduce noise and improve defect capture. In this manner, for defects embedded in regular structures that fluoresce but scatter less than the defects scatter light, insertion into the imaging path of a spectral filter centered on the illumination wavelength that excludes fluorescence emission from the regular wafer pattern may increase the signal-to-noise ratio for the defects. Additionally, the design of these filters will include rejection of stray light sources on the tool, including the auto-focus system and out-of-system-band wavelengths produced by the illuminator. In this way, the detection becomes highly selective and quantitative, augmenting not only the signal-to-noise ratio of the specific defect(s) of interest, but also supplying additional information such as defect material and dimensions as described further herein.

In one embodiment, the detection subsystem includes two or more channels configured to separately and simultaneously detect the fluorescence or the non-fluorescent light from the wafer in different wavelength ranges. For example, the systems can be configured to include multiple parallel imaging channels that image varying wavelength ranges through suitable selection of dichroic and bandpass filter components, possibly improving the throughput of the system. In the embodiment shown in FIG. 1, one of the channels may include bandpass filter(s) 114 and detector 116 and the other of the channels may include bandpass filter(s) 118 and detector 120. In addition, the system may include more than two channels (e.g., by insertion of one or more additional beamsplitters (not shown) into the path of the light from the wafer, each of which may be coupled to a detector (not shown) and possibly spectral filters (not shown) and/or other optical elements (not shown)).

In one such embodiment, one of the two or more channels is configured to detect only the fluorescence, and another of the two or more channels is configured to detect the non-fluorescent light from the wafer without detecting the fluorescence. For example, the channel including bandpass filters(s) 114 and detector 116 may be configured to detect only fluorescence from wafer 110, and the channel that includes bandpass filter(s) 118 and detector 120 may be configured to detect the non-fluorescent light from the wafer without detecting the fluorescence. In this manner, one channel may detect fluorescence, and the other channel may detect light other than fluorescence. As such, fluorescence and light other than fluorescence may be detected separately and simultaneously.

In another such embodiment, one of the two or more channels is configured to detect only the fluorescence in a first wavelength band, and another of the two or more channels is configured to detect only the fluorescence in a second wavelength band different than the first wavelength band. For example, the channel including bandpass filters(s) 114 and detector 116 may be configured to detect fluorescence in a first wavelength band, and the channel that includes bandpass filter(s) 118 and detector 120 may be configured to detect fluorescence in a second wavelength band. In this manner, different wavelength ranges of fluorescence may be detected by different channels simultaneously. In addition, the different fluorescence wavelength ranges may be mutually exclusive (e.g., separated by one or more wavelengths) or may overlap entirely (e.g., one wavelength range may be entirely within another wavelength range) or partially (e.g., multiple wavelength ranges may include the same one or more wavelengths, but at least some of the wavelengths in a first wavelength range are mutually exclusive of at least some of the wavelengths in a second wavelength range, and vice versa).

In some embodiments, the detection subsystem includes a spectrometer configured to measure a characteristic of the fluorescence or the non-fluorescent light from the wafer across a wavelength range. For example, in the embodiment shown in FIG. 1, one or more of detectors 116 and 120 may be a spectrometer. In this manner, to further characterize wafer materials by measuring the fluorescence emission spectrum, the system could incorporate a spectrometer possibly for review mode.

As described above, the detection subsystem may be configured to selectively and separately detect the light from the wafer based on the wavelength of the light thereby selectively and separately detecting fluorescence and non-fluorescent light from the wafer. In a similar manner, if the illumination subsystem is configured for selective illumination angle and/or polarization, the detection subsystem may be configured for selective detection of light based on angle from the wafer (or collection angle) and/or polarization. For example, the detection subsystem may include one or more apertures that can be used to control the collection angles of the light detected by the detection subsystem. In another example, the detection subsystem may include one or more polarizing components in the path of the light from the wafer that can be used to control the polarizations of the light detected by the detection subsystem. As described further above, the selective detection of light from the wafer based on illumination angle and/or polarization can be used to complement the separate and selective detection of fluorescence and non-fluorescent light for wafer defect detection.

The system also includes a computer subsystem configured to determine information for defects on the wafer using output generated by the detection subsystem responsive to the detected fluorescence or the detected non-fluorescent light. For example, in the embodiment shown in FIG. 1, the system may include computer subsystem 122, which may be coupled to detectors 116 and 120 by one or more transmission media shown in FIG. 1 by the dashed lines, which may include "wired" and/or "wireless" transmission media, such that the computer subsystem can receive output generated by the detectors of the detection subsystem that is responsive to the detected fluorescence or the detected non-fluorescent light. The output of the detectors may include, for example, signals, images, data, image data, and the like. The computer subsystem may be further configured as described herein. The information may be defects on the wafer, material discrimination, and defect classification. The information may include one or more of data, image data, images, and any other form in which such information can be output. The information may be stored in or output as an inspection results file or defect review results file.

One main advantage of the embodiments described herein is an augmented capture rate, sensitivity, material discrimination, and classification of the defects of interest for patterned wafer inspection and review. In one embodiment, the computer subsystem is configured to determine a composition of the defects, the one or more materials, or the wafer based on one or more wavelengths in an emission spectra of the detected fluorescence. For example, in traditional inspection, scattered waves are at the same wavelength as illumination ("elastic scattering"). But in fluorescence, emission occurs at longer wavelengths, allowing potential discrimination of materials with different fluorescent properties. Determining the composition of the one or more materials or the wafer may include monitoring for damage or photo-bleaching of wafers. For example, if the intended composition of one or more materials on a wafer is known to cause the one or more materials to fluorescence, then fluorescence can be used as a measure of the composition of the one or more materials. In particular, photo-bleaching occurs when a fluorescence molecule permanently loses the ability to emit photons under light excitation, i.e., it does not fluoresce any more. Photo-bleaching is due to a photo-induced chemical modification of the fluorescent molecule, either forming covalent bonds with other molecules and/or modifying irreversibly the chemical structure of the original fluorescent molecule due to damage. The amount of excitation-photo emission-decay to ground state cycles is determined by the actual molecular structure and/or by the environment in which the molecule is located. For instance, an environment full of oxygen will increase the probability of photo-bleaching. Therefore, if a material known to fluoresce does not emit any measurable fluorescence, it can be determined that the composition of the material has changed from the intended composition. Quenching is another way in which the amount of fluorescence emitted by a fluorescing molecule is diminished. Quenching is due to either collision with other molecules or forming more stable compounds with other species. In both situations, fluorescence is greatly reduced. As such, if the amount of fluorescence measured for a material is less than expected, the composition of the material may be determined to be different from the intended composition and it may be determined that quenching may have occurred.

In another embodiment, the computer subsystem is configured to determine a composition of the defects, the one or more materials, or the wafer based on a peak intensity of the fluorescence in an emission spectra. For example, fluorescing materials such as oxides, nitrides, and resists have broad emission spectra, but with different peak intensities. Therefore, narrow spectral filtering helps to discriminate the nature of defects, which is related to the specific fabrication process that created them.

In some embodiments, the computer subsystem is configured to detect a defect on the wafer based on the output, determine a width of an emission spectra of the fluorescence corresponding to the defect, and determine a size of the defect based on the width of the emission spectra. For example, the emission spectrum becomes narrower the more a defect approaches the quantum confinement, the more the defect is small, since less excited state is available. Therefore, measuring the width of the spectrum might give an indication of how small the defect is.

In another embodiment, the one or more illumination wavelengths include different excitation wavelengths, and the illumination subsystem is configured to separately direct the different excitation wavelengths to the wafer. For example, the illumination subsystem may include a broadband light source as described above that is configured to generate light at different wavelengths and different excitation wavelengths and one or more spectral filters that can be positioned independently in the path of the light from the light source such that depending on which spectral filter is positioned in the path of the light, different excitation wavelength(s) can be directed to the wafer, one wavelength or wavelength range at a time. In one such embodiment, the detection subsystem is configured to separately detect the fluorescence from the one or more materials due to the different excitation wavelengths, and the computer subsystem is configured to determine a composition of the one or more materials based on which of the different excitation wavelengths caused the fluorescence from the one or more materials. In this manner, the embodiments provide a method for characterizing defect or wafer composition through measurement of the wafer's excitation and emission spectra. For example, the excitation spectrum is different for different materials. Therefore, control of the illumination wavelength range can aid in discrimination of the defect or wafer pattern composition.

In another embodiment, the wafer is a patterned wafer, and the detection subsystem or the computer subsystem is configured to remove output responsive to patterned features on the wafer from the output generated by the detection subsystem. For example, in some instances, the patterned features may not emit fluorescence while defects of interest do. Therefore, by detecting only fluorescence from the wafer, the detection subsystem can remove output responsive to the patterned features from the output. However, in some instances, the detection subsystem or the computer subsystem may be configured to remove the output responsive to the patterned features by Fourier or other spatial filtering that is performed optically by the detection subsystem or electronically by the computer subsystem. Such spatial filtering can be performed in any suitable manner and may be performed in combination with the filtering performed based on the emission wavelength of the detected light thereby reducing noise in the output by a variety of methods.

In some embodiments, the output generated by the detection subsystem includes images of the wafer. For example, the detector(s) of the detection subsystem described above may be imaging detectors that are configured to capture image(s) of the wafer. Therefore, the output generated by the detection subsystem may include images.

In another embodiment, the wafer is a patterned wafer, the defects are fluorescing defects, and the detection subsystem is configured to detect only the fluorescence from the defects on the wafer without detecting the non-fluorescent light from patterned features on the wafer. In this manner, the systems can be configured to detect defects on patterned wafers and multiple layer patterned wafers. For example, the system configurations described herein provide control of both the illumination and detection wavelengths primarily to differentiate defects from regular wafer patterns. In one configuration described above, fluorescence from a regular wafer pattern can be excluded from a detected image by inserting into the imaging path a bandpass filter centered on the excitation wavelength. Therefore, one main advantage of the embodiments described herein is an augmented capture rate, sensitivity, material discrimination, and classification of the defects of interest for patterned wafer inspection and review. The embodiments described herein enable detection or rejection of fluorescence with an independent method to remove the contribution of regular patterns from the detected signals or images. Many common wafer materials fluoresce when excited by DUV or UV light, such as resist, BARC, $SiO_2$, and SiN whereas other common wafer materials do not fluoresce or fluoresce minimally, such as metals, Si, and polysilicon. Metals scatter light very efficiently whereas oxides, nitrides, and resists scatter weakly compared to metals. Many inspection points contain multiple layers of varying patterned materials. The embodiments described herein may improve the sensitivity of inspection systems for after develop inspection (ADI) and oxide etch inspections, which are historically difficult for optical inspection methods. For example, one such point, ADI can include inspection of a wafer that has patterned resist on top of transparent films (e.g., BARC and oxide), which in turn lie above a patterned structure that includes metal or semiconductor patterns separated by oxide. Light scattered from the metal lines often dominates signals arising from defects in the resist. Spectrally filtering the light scattered by metals, which has the same wavelength as the illumination, and detecting the fluorescence from the defect can augment the overall signal-to-noise ratio (SNR) and improve defect detection. This method may detect defects embedded in a multi-layer wafer structure if the defect fluoresces and the surrounding wafer structure fluoresces less, as might be the case for resist residues at the bottom of trenches.

Figure 2:
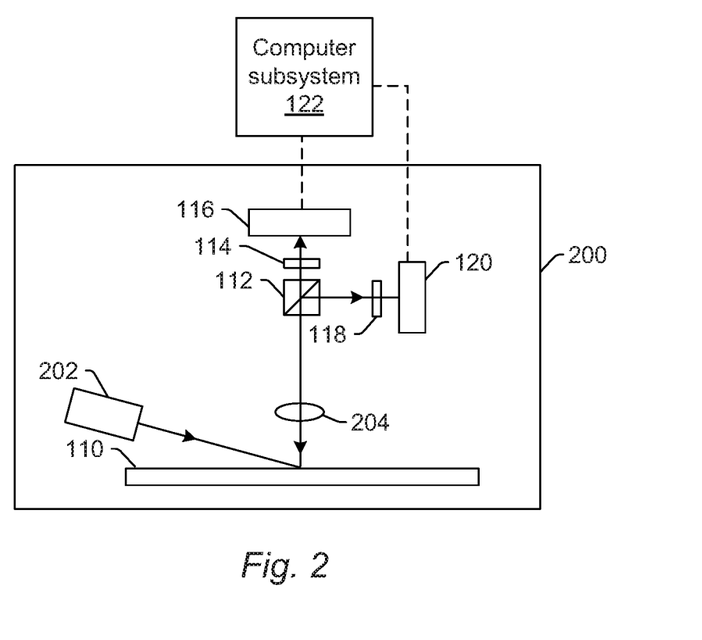

A system configured to determine information for defects on a wafer may also be implemented using a quasi-monochromatic light source in the excitation path that illuminates the patterned structure without passing through detection optics (in a dark field like scheme). In this configuration, the excitation dichroic mirror or beamsplitter (e.g., beamsplitter 106) and illumination filters (e.g., spectral filter(s) 104) described above can be removed and the detection objective simplified. For example, in one embodiment shown in FIG. 2, the illumination subsystem of system 200 may include light source 202 that may be a quasi-monochromatic light source that is configured to direct light onto wafer 110 at an oblique angle of incidence. One or more other optical elements (not shown) such as a focusing lens may be positioned in the path of the light from light source 202. Light from the wafer due to illumination may be collected by objective 204 of the detection subsystem of this system that may be configured as described above with respect to objective 108. However, objective 204 may be simpler than objective 108. Light from the objective may be directed to beamsplitter 112 of the detection subsystem, which may be configured as described above. As shown in FIG. 2, the detection subsystem of this embodiment may also include spectral filter(s) 114, detector 116, spectral filter(s) 118, and detector 120, which may be configured as described above. The system shown in FIG. 2 may be further configured as described herein. For example, as shown in FIG. 2, the system may include computer subsystem 122 that may be further configured as described herein.

Such an implementation can be realized on a modified dark field inspection tool such as the 9xxx series of tools, which are commercially available from KLA-Tencor, if the collection optics of such tools were modified to accommodate a broader wavelength range. The systems described herein can also be configured for a dark field flood illumination imaging system. For this concept, because fluorescence frequently occurs at wavelengths longer than 250 nm, the imaging objective may be easier and cheaper to manufacture compared to broadband DUV objectives. Along these lines, platforms of commercially available systems such as the 236x tools commercially available from KLA-Tencor could be modified to include outside the objective illumination using DUV and UV laser sources. This would limit selecting the illumination wavelength based on the excitation spectra of the material, but it could increase the amount of light delivered to the wafer resulting in an increase in the fluorescence signal.

It is noted that FIGS. 1 and 2 are provided herein to generally illustrate some configurations of the system embodiments described herein. Obviously, the system configurations described herein may be altered to optimize the performance of the system as is normally performed when designing a commercial inspection or review system. In addition, the systems described herein may be implemented using an existing inspection system (e.g., by adding functionality described herein to an existing inspection system) such as the 29xx/28xx and 236x series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

The systems described above are, therefore, different from currently available wafer inspection systems in a number of important ways. For example, some currently available inspection systems contain spectral filters to either detect or suppress fluorescence signals from defects or wafer background respectively. These tools are configured for only a single illumination wavelength and contain a limited selection of spectral filters in the collection path. Generally, the tools contain two collection path filters: one filter that passes only the illumination wavelength to exclude fluorescence from the wafer background and one filter that blocks the illumination wavelength to enable detection of fluorescence from defects.

Some inspection tools are also limited in their ability to remove contributions from rectilinear patterns from the detected signals. Furthermore, some inspection tools do not provide high resolution microscopic imaging. While some tools are designed to remove regular wafer patterns from images (e.g., die-to-die or cell-to-cell subtraction or Fourier filtering), these tools are currently not configured to detect only or exclude only fluorescence from either defects or regular patterns. In addition, although some inspection systems are configured to detect fluorescence signals instead of signals at the wavelength of illumination, such systems are not configured to detect fluorescence signals from defects to improve signal-to-noise, where noise originates from non-fluorescing regular wafer structures. In addition, many systems are not configured for tuning the incident waveband or measuring the emission spectra to determine wafer or defect composition.

Each of the system embodiments described above may be configured to perform any step(s) of any method(s) described herein. In addition, each of the system embodiments described herein may be configured according to any other embodiments or systems described herein.

Another embodiment relates to a method for determining information for defects on a wafer. The method includes directing light having one or more illumination wavelengths to a wafer. The one or more illumination wavelengths are selected to cause fluorescence from one or more materials on the wafer without causing fluorescence from one or more other materials on the wafer. The directing step may be performed using any of the illumination subsystems described herein. The method also includes detecting only the fluorescence from the one or more materials or detecting non-fluorescent light from the wafer without detecting the fluorescence from the one or more materials. Detecting only the fluorescence or detecting the non-fluorescent light may be performed using any of the detection subsystems described herein. In addition, the method includes determining information for defects on the wafer using output responsive to the detected fluorescence or the detected non-fluorescent light, which may be performed as described further herein using any of the computer subsystems described herein.

In one embodiment, the wafer is a patterned wafer, and the method includes performing the directing and detecting steps using an unpatterned wafer to determine the one or more illumination wavelengths used for the patterned wafer and one or more wavelengths of the fluorescence or the non-fluorescent light from the patterned wafer detected in the detecting step performed for the patterned wafer. For example, the systems and methods described herein could be used to initially characterize the excitation and emission spectra of unpatterned wafer films and then to use these measurements to set the illumination and imaging wavebands for patterned wafer inspection.

Each of the embodiments of the method described above may include any other step(s) of any other method(s) described herein. In addition, each of the embodiments of the method described above may be performed by any of the systems described herein.

Figure 3:
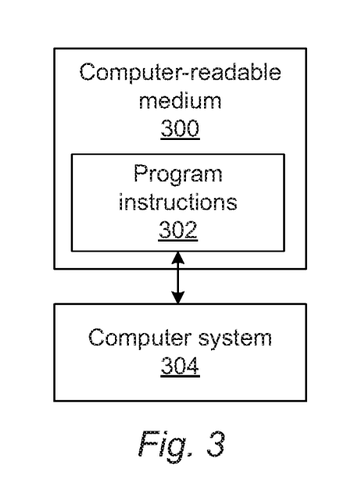
FIG. 3 is a block diagram illustrating one embodiment of a non-transitory computer-readable medium.

Another embodiment relates to a non-transitory computer-readable medium containing program instructions stored therein for causing a computer system to perform a computer-implemented method for determining information for defects on a wafer. One embodiment of such a computer-readable medium is shown in FIG. 3. In particular, computer-readable medium 300 contains program instructions 302 stored therein for causing computer system 304 to perform a computer-implemented method for determining information for defects on a wafer. The computer-implemented method includes any step(s) described above with respect to the computer subsystem of the system. In addition, the computer-readable medium may be further configured as described herein.

Program instructions 302 implementing methods such as those described herein may be stored on computer-readable medium 300. The computer-readable medium may be a non-transitory computer-readable storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

Computer system 304 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

Further modifications and alternative embodiments of various aspects of the invention will be apparent to those skilled in the art in view of this description. For example, systems and methods for determining information for defects on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to determine information for defects on a wafer, comprising:
   an illumination subsystem configured to direct light having one or more illumination wavelengths to a wafer, wherein the one or more illumination wavelengths are selected to cause fluorescence from one or more materials on the wafer without causing fluorescence from one or more other materials on the wafer;
   a detection subsystem configured to detect the fluorescence from the one or more materials and to detect non-fluorescent light from the wafer without detecting the fluorescence from the one or more materials, wherein the detection subsystem comprises two or more channels configured to separately and simultaneously detect the fluorescence and the non-fluorescent light from the wafer, and wherein one of the two or more channels detects only the fluorescence while another of the two or more channels detects the non-fluorescent light from the wafer without detecting the fluorescence; and
   a computer subsystem configured to determine information for defects on the wafer using output generated by the detection subsystem responsive to the detected fluorescence and the detected non-fluorescent light.

2. The system of claim 1, wherein the computer subsystem is further configured to determine a composition of the defects, the one or more materials, or the wafer based on one or more wavelengths in an emission spectra of the detected fluorescence.

3. The system of claim 1, wherein the computer subsystem is further configured to determine a composition of the defects, the one or more materials, or the wafer based on a peak intensity of the fluorescence in an emission spectra.

4. The system of claim 1, wherein the computer subsystem is further configured to detect a defect on the wafer based on the output, determine a width of an emission spectra of the fluorescence corresponding to the defect, and determine a size of the defect based on the width of the emission spectra.

5. The system of claim 1, wherein the one or more illumination wavelengths comprise different excitation wavelengths, wherein the illumination subsystem is further configured to separately direct the different excitation wavelengths to the wafer, wherein the detection subsystem is further configured to separately detect the fluorescence from the one or more materials due to the different excitation wavelengths, and wherein the computer subsystem is further configured to determine a composition of the one or more materials based on which of the different excitation wavelengths caused the fluorescence from the one or more materials.

6. The system of claim 1, wherein the wafer is a patterned wafer, and wherein the detection subsystem or the computer subsystem is further configured to remove output responsive to patterned features on the wafer from the output generated by the detection subsystem.

7. The system of claim 1, wherein the output generated by the detection subsystem comprises images of the wafer.

8. The system of claim 1, wherein the wafer is a patterned wafer, wherein the defects are fluorescing defects, and wherein the one of the two or more channels is further configured to detect only the fluorescence from the defects on the wafer without detecting the non-fluorescent light from patterned features on the wafer.

9. The system of claim 1, wherein one or more wavelengths of the fluorescence and the non-fluorescent light detected by the detection subsystem are selected by altering one or more parameters of the detection subsystem based on the one or more materials, the defects, the wafer, or some combination thereof.

10. The system of claim 1, wherein the illumination and detection subsystems comprise a common objective lens and a common dichroic mirror or beamsplitter, and wherein the common objective lens and the common dichroic mirror or beamsplitter are configured to direct the light from a light source of the illumination subsystem to the wafer and to direct the fluorescence and the non-fluorescent light from the wafer to detectors of the one and the other of the two or more channels, respectively.

11. The system of claim 1, wherein the detection subsystem further comprises one or more bandpass filters positioned in a path of the fluorescence and the non-fluorescent light from the wafer, and wherein the one or more bandpass filters are configured to control the fluorescence detected by the one of the two or more channels and the non-fluorescent light detected by the other of the two or more channels.

12. The system of claim 1, wherein the illumination subsystem comprises a broadband light source and one or more spectral filters positioned in a path of light from the broadband light source.

13. The system of claim 12, wherein the one or more spectral filters comprise one or more interference filters.

14. The system of claim 1, wherein the illumination subsystem comprises one or more narrowband light sources.

15. The system of claim 1, wherein the illumination subsystem comprises one or more laser light sources.

16. The system of claim 1, wherein the one of the two or more channels is further configured to separately and simultaneously detect the fluorescence from the wafer in different wavelength ranges, and wherein the other of the two or more channels is further configured to separately and simultaneously detect the non-fluorescent light from the wafer in different wavelength ranges.

17. The system of claim 16, wherein the one of the two or more channels comprises a first channel and a second channel, wherein the first channel is configured to detect only the fluorescence in a first wavelength band, and wherein the second channel is further configured to detect only the fluorescence in a second wavelength band different than the first wavelength band.

18. The system of claim 1, wherein the one or the other of the two or more channels comprises a spectrometer configured to measure a characteristic of the fluorescence or the non-fluorescent light, respectively, from the wafer across a wavelength range.

19. A method for determining information for defects on a wafer, comprising:
   directing light having one or more illumination wavelengths to a wafer, wherein the one or more illumination wavelengths are selected to cause fluorescence from one or more materials on the wafer without causing fluorescence from one or more other materials on the wafer;
   detecting the fluorescence from the one or more materials and detecting non-fluorescent light from the wafer without detecting the fluorescence from the one or more materials with a detection subsystem, wherein the detection subsystem comprises two or more channels configured to separately and simultaneously detect the fluorescence and the non-fluorescent light from the wafer, and wherein one of the two or more channels detects only the fluorescence while another of the two or more channels detects the non-fluorescent light from the wafer without detecting the fluorescence; and
   determining information for defects on the wafer using output responsive to the detected fluorescence and the detected non-fluorescent light.

20. The method of claim 19, wherein the wafer is a patterned wafer, the method further comprising performing the directing and detecting steps using an unpatterned wafer to determine the one or more illumination wavelengths used for the patterned wafer and one or more wavelengths of the fluorescence and the non-fluorescent light from the patterned wafer detected in the detecting step performed for the patterned wafer.

* * * * *